US009056117B2

United States Patent
Saxena

(10) Patent No.: US 9,056,117 B2
(45) Date of Patent: Jun. 16, 2015

(54) HERBAL FORMULATION FOR WOUND HEALING

(75) Inventor: Manish Saxena, New Delhi (IN)

(73) Assignee: SUNEV PHARMA SOLUTIONS LTD., Chandigarh (IN)

( * ) Notice: Subject to any disclaimer, the term of this patent is extended or adjusted under 35 U.S.C. 154(b) by 1148 days.

(21) Appl. No.: 12/519,137

(22) PCT Filed: Nov. 28, 2007

(86) PCT No.: PCT/IN2007/000557
§ 371 (c)(1),
(2), (4) Date: Mar. 25, 2010

(87) PCT Pub. No.: WO2008/072256
PCT Pub. Date: Jun. 19, 2008

(65) Prior Publication Data
US 2010/0178367 A1    Jul. 15, 2010

(30) Foreign Application Priority Data

Dec. 12, 2006   (IN) .......................... 2648/DEL/2006

(51) Int. Cl.
*A61K 36/61*    (2006.01)
*A61K 36/58*    (2006.01)
(52) U.S. Cl.
CPC ...................................... *A61K 36/58* (2013.01)
(58) Field of Classification Search
CPC .............................. A61K 36/61; A01N 65/00
See application file for complete search history.

(56) References Cited

U.S. PATENT DOCUMENTS

| | | | |
|---|---|---|---|
| 5,693,327 A | 12/1997 | Shah | |
| 5,897,865 A * | 4/1999 | Nguyen | ........................ 424/756 |
| 2006/0134229 A1 | 6/2006 | Li et al. | |

FOREIGN PATENT DOCUMENTS

| | | |
|---|---|---|
| DE | 10019670 A1 | 10/2001 |
| FR | 2101244 A | 3/1972 |
| GB | 1314136 | 4/1973 |
| GB | 2314269 A | 12/1997 |
| HU | 9904431 A1 | 7/2001 |
| WO | WO 0033855 A1 * | 6/2000 |
| WO | 2005115090 A2 | 12/2005 |
| ZA | 9802679 A | 9/1998 |
| ZA | 9803753 A | 11/1999 |

OTHER PUBLICATIONS

Haridredyagh"tam. From: Vindamedhava;—Marathi translated by Datto vallala Borkar;Yagyeswara Gopal Dixit, Bookseller, Pune;Edn. 1922, p. 152; Cakradatta—Translated by Indradeva Tripathi; Chaukhamba Sanskrit Samsthan (Varanasi), Ed. 4th 2002, p. 83 (three sources provided at the bottom of the page—two are written here).*

Jatyadi Tailam. From: Rasak¢madhenu Sa¼hit¢—Edited by Jivaramakalidasa Sastri, Part 4, Chaukhambha Publishers, Varanasi, Edn. 1st 1992 [Retrieved from the Internet: Nov. 6, 2011]. Retrieved from: TKDL website <URL: http://www.tkdl.res.in>.*
Suguna et al. "Influence of *Terminalia chebula* on Dermal Wound Healing in Rats". Phytotherapy Research Phytother. Res. 16, 227-231 (2002).*
Tiladi Yoga. From: Va-gasena—Commentator Shaligram Vaisya, Edited Shankar Ialji Jain; Khermraj Shikrishna Das Prakashan, Bombay, Edn 1996. [Retrieved from the Internet: Nov. 6, 2011]. Retrieved from: TKDL website <URL: http://www.tkdl.res.in>.*
Bal¢dyagh"tam. Rasaratn¢kara²-Rasendra kha'²am Comm. Datto Vall¢l Borakara, Ed. 2nd 1986, Shri Gaj¢nan Book Depot, (Pune), p. 599 [Retrieved from the Internet on: Apr. 5, 2012]. Retrieved from the Internet: TKDL website.*
"Coconut-info". Internet Archive Date: Aug. 6, 2002 [Retrieved from the Internet on: Apr. 5, 2012]. Retrieved from the Internet: <URL: http://web.archive.org/web/20020806081633/http://www.coconut-info.com/virgin_coconut_Oil_for_your_skin.html>.*
Bandyopadhyay et al., "Clinical studies on the effect of Neem (*Azadirachta indica*) bark extract on gastric secretion and gastroduodenal ulcer," Life Sciences, 2004, pp. 2867-2878, vol. 75, Elsevier, Netherlands.
Anonymous, "AMPUCARE: Clinical Studies," Internet Article, retrieved from: http://www.ampucare.com/clinical_studies_link1.pdf on Feb. 28, 2008.
Chaudhary et al., "Clinical trial survey report of ampucare done on patients with different wounds," Journal of Ecophysiological Occupational Health, 2008, pp. 89-97, vol. 8, The Academy of Environmental Biology, India.
Chaudhary et al., "A Study to Evaluate Dermal Sensitization Potential of AMPUCARE," Life Science Bulletin, 2008, pp. 51-54, vol. 5, iss.1.
Chaudhary et al., "Safety Evaluation for Ocular Irritation of AMPUCARE seen on Himalayan Albino Rabbits," National Journal of Life Sciences, 2008, pp. 127-130, vol. 5, iss.1.
Chaudhary et al., "Toxicological evaluation of ampucare: acute oral toxicity in Wistar rats," Journal of Ecophysiological Occupational Health, 2008, pp. 27-30, vol. 8, The Academy of Environmental Biology, India.
Chaudhary et al., "A Study to Evaluate the Presence of Lead, Cadmium, Chromium and Nickel in a Polyherbal Preparation—AMPUCARE," (unpublished).

(Continued)

*Primary Examiner* — Amy L Clark
(74) *Attorney, Agent, or Firm* — Hultquist, PLLC; Steven J. Hultquist; Mary B. Grant

(57) ABSTRACT

The present invention pertains to a herbal formulation with highly potent wound healing properties, in humans and animals. The composition consists of aqueous extracts of *Azadirachta indica*, in a mixture of natural oils along with herbs viz. *Berberis aristata, Curcuma longa, Glycyrrhiza glabra, Jasminum officinale, Picrorhiza kurrooa, Pongamia pinnata, Rubia folia, Saussurea lappa, Terminalia chebula, Trichosanthes dioica, Capsicum* and *Stellata wild* in well-defined ratios. The invention also includes a process for preparing the formulation by extracting the water-soluble components from bark of *Azadirachta indica*.

8 Claims, No Drawings

(56) References Cited

OTHER PUBLICATIONS

Chaudhary et al., "Quality Assessment of Major Ingredients of AMPUCARE by Physico-chemical Parameters," (unpublished).

Naithani et al., "Spectrophotometric Estimation of Curcumin in *Curcuma longa* Procured from Different Zones of India," Journal of Nature Conservation, 2008, pp. 263-267, vol. 20, iss.2, Nature Conservators, India.

Chaudhary et al., "Acute Dermal Irritation Studies of AMPUCARE Dose on Himalayan Albino Rabbits," National Journal of Life Sciences, 2008, pp. 285-286, vol. 5, iss.2.

Bussmann, R., et al., "Plant use of the Maasai of Sekenani Valley, Maasai Mara, Kenya", "Journal of Ethnobiology and Ethnomedicine", May 5, 2006, vol. 2, No. 22.

Ignacimuthu, S., et al., "Ethnobotanical investigations among tribes in Madurai District of Tamil Nadu (India)", "Journal of Ethnobiology and Ethnomedicine", May 11, 2006, vol. 2, No. 25.

Khan, S., et al., "Therapeutic Plants of Ayurveda: A Review of Selected Clinical and Other Studies for 166 Species", "The Journal of Alternative and Complementary Medicine", Oct. 2001, pp. 405-515, vol. 7, No. 5.

Kim, K., et al., "Antibacterial Activity of *Curcuma longa* L. Against Methicillin-Resistant *Staphylococcus aureus*.", "Phytother. Res.", Jul. 2005, pp. 599-604 (Abstract), vol. 19, No. 7.

Muthu, C., et al., "Medicinal plants used by traditional healers in Kancheepuram District of Tamil Nadu, India", "Journal of Ethnobiology and Ethnomedicine", Oct. 7, 2006, vol. 2, No. 43.

Rajesh, M., et al., "Protective Activity of *Glycyrrhiza glabra* Linn. on Carbon Tetrachloride-Induced Peroxidative Damage", "Indian J. Pharmacol.", Oct. 2004, pp. 284-287, vol. 36, No. 5.

Yesilada, E., et al., "*Berberis crataegina* DC. Root Exhibits Potent Anti-Inflammatory, Analgesic and Febrifuge Effects in Mice and Rats.", "J. Ethnopharmacol.", Feb. 2002, pp. 237-248 (Abstract), vol. 79, No. 2.

\* cited by examiner

HERBAL FORMULATION FOR WOUND HEALING

FIELD OF INVENTION

The present invention relates to the field of herbal formulations having therapeutic properties. More specifically, it relates to a herbal formulation having potent antimicrobial, anti fungal and wound healing properties, which is quite effective in curing external wounds of any nature in humans, especially non-healing wounds of diabetics and wounds referred to as 'bed sores'. The herbal formulation is also quite effective in treating wounds in animals.

BACKGROUND OF THE INVENTION

As is well-known in the prior art, usual methods for the cure of wounds whether in humans or animals, involve certain well-defined steps. These are curettage (removal of dead/infected tissues), disinfection (with disinfectants containing either iodine or hydrogen peroxide) and antibiotic therapy (either local or systemic, in form of powder, cream or spray). Lastly, to avoid hardening of the skin and crust formation, gauzes soaked in fatty humecants based on Vaseline, silicone oils or glycerol are applied. Dressing of the wound with sterile gauze is usually carried out not only to prevent exposure of the wound to infectious agents e.g. bacteria present in the environment, but also to soak exudations and secretions from the wound. These bandages need to be removed at regular intervals. In poor hygienic or environmental conditions e.g. those frequently present in developing countries, the wounds cannot be managed adequately and remain exposed to dust and environmental infestations which can contribute to important infections of the wound.

Despite efficacious anti-microbial treatment and improved supportive measures, wound treatment still poses immense challenges. Treatment and cure for invasive infections, blunt injuries, burns caused by electrical or chemical accidents, radiation burns and the like, is not very effective and leaves much to be desired. In fact, introduction of clinically effective anti-microbial agents has resulted in the rapid emergence of strains of bacteria resistant to such agents.

In countries with aging populations e.g the Unites States, leg ulcers in patients pose major challenges. An estimated 2 million workdays are lost in the US because of leg ulcers. Apart from loss of man days, cost of treating these non-healing wounds can be tremendous. The prevalence of pressure ulcers (pressure sores or 'bed' sores) of the lower body in the elderly has been estimated to be 3-11%. The morbidity and mortality associated with pressure ulcers is significant. The death rate in patients with pressure ulcers is four fold greater than those without. In addition, septic elderly patients with pressure ulcers have a hospital mortality rate in excess of 50%. Treatment costs can be expensive owing to inclusion of intensive nursing care as well as adjunctive therapies e.g. anti pressure devices, protective dressings and skin treatments.

Wounds of diabetics are practically unmanageable and are usually regarded as 'incurable'. In fact, diabetes is an important underlying condition in leg ulcers. Various therapies for the treatment of leg ulcers e.g. multi-layer compression-bandage systems, topical recombinant human platelet derived growth factor, human skin equivalent for skin grafting etc. are available which may aid in wound healing. However, these therapies are expensive and may be cost prohibitive for many patients. Quite often inability to treat wounds leads to amputation of the infected limbs. Wound management in animals poses additional challenges. Unlike humans, chances of exposure of wounds to environmental infestations, in case of animals are much higher. Of particular concern are attacks by flies especially myiasigenic flies (sarcophagidae, callyphoridae) or any other flies (muscidae) which can aggravate wounds and lead to complications. To prevent infestations by flies, a common practice adopted in case of wounded animals is pouring creolina (mixture of phenols and tar) on the wounded area. This remedy though well-entrenched in animal husbandry, has serious limitations and disadvantages. Not only is it tissue damaging and toxic, but its 'insect protecting or repelling' action is very short-lived—barely half an hour! Another animal husbandry practice involves direct use of insecticides on the maggot infected wounds or sores. Apart from risk of acute or chronic intoxication of the animals, the practice poses environmental threat and also risk of contamination of the food chain, if the animals are involved in products for human consumption e.g. meat or milk. The present invention eliminates all such risks.

Wound healing and management, whether in humans or animals thus poses serious challenges. Existing therapies of modern science have limitations when it comes to treatment and cure of certain wounds. In animals, wounds and lesions pose practical challenges especially under tropical conditions of high temperature and humidity when flies become very active. Such conditions also affect wound treatment in humans, especially in developing countries, where hygienic conditions are very often completely inadequate. The risk of complications due to parasites, bacteria etc. are a harsh reality, especially for weak and undernourished subjects, especially children.

The present invention provides a novel herbal composition comprising aqueous extracts of neem bark along with several herbs in a mixture of natural oils. The composition which is meant for external or topical application only, exhibits remarkable antibiotic and wound-healing properties. It is particularly effective in treating and curing wounds, which are regarded as 'incurable' in state of the art. The potency and powerful antimicrobial action of the herbal formulation is due to the synergistic action of the components, mainly plant extracts, present in it.

The present invention provides an effective and low cost method for treatment of wounds and sores.

PRIOR ART DISCUSSION

A number of herbal formulations for wound healing and injuries have been described in the prior art. US patent application no. 2006/0134229 discloses a herbal formulation consisting of the organic extract of the plant—*Geum Japonicum Thunb* variant. The invention is specifically directed for the cure of skeletal muscle injuries and soft tissue healing and not that of wounds.

PCT application no. WO2005/115090 A2 discloses a herbal composition having potent antimicrobial and wound healing properties. The composition contains extracts of only *Ficus* species along with *Azadirachta indica*, prepared by use of aqueous as well as organic solvents in admixture with pharmaceutically acceptable carriers, excipients and adjuvants. Use of bark of the respective plants is emphasized. No other component is added in the herbal composition in the described invention.

SUMMARY OF THE INVENTION

According to the present invention a novel herbal formulation is provided for external or topical application, for the treatment and cure of all types of wounds and lesions in humans and animals. The herbal formulation consists of aqueous extracts of neem bark, in a mixture of natural oils along with several herbs, in well-defined ratios. The composition exhibits remarkable efficacy in treating and curing wounds, which are regarded as 'incurable' in state of the art. The herbal formulation was arrived at by carrying out meticulous studies by the inventor, to identify the most effective and active combination of plant extracts in wound care.

OBJECTS OF THE INVENTION

It is a general objective of the invention to provide a novel herbal formulation for wound healing and its method of manufacture. Yet another objective is to provide a herbal formulation which provides an inexpensive alternative wound healing therapy, which does not have undesirable side-effects. Another objective of the present invention is to disclose a herbal formulation which is easy to manufacture.

DETAILED DESCRIPTION OF THE PREFERRED EMBODIMENT

The invention describes a herbal wound healing formulation which is used to treat different types of wounds/injuries in humans and animals and helps in preventing amputations.

Another embodiment of the invention is that the formulation improves blood flow and has immuno-modulatory properties in addition to being anti bacterial, anti-fungal, anti inflammatory and analgesic. The formulation is also useful for treating infections and chronic non healing wounds like diabetic foot ulcer, dry and wet gangrene, venous ulcer, varicose veins, war wounds, burn wounds, post operative situation and the like.

Another embodiment of the invention is that the formulation acts by applying it topically e.g skin applications and or externally (eye/ear/nasal drops, gynaecological applications etc).

Representative adjuncts include copper sulphate as a preservative, bee wax as a thickening agent, activated charcoal and/or Fuller's earth as decolorizing agents, calcium-D-saccharate, serolite, bentonite and magnesium oxide.

Another embodiment of the invention, is a composition of the formulation composed of an aqueous extract, a oil-herbs mix along with other adjuncts.
 a) The aqueous part consists of an aqueous extract of the bark of *Azadirachta indica* in the range 4-7%, preferably 6% in water.
 b) The oil-herbs mix consists of a mixture of four oils viz. castor, mustard, coconut and black sesame in equal ratios, along with twelve herbs in the range of 0.5-4% preferably 1% viz. *Berberis aristata* or *Berberis vulgaris*, *Curcuma longa* (6-9%, preferably 7%), *Glycyrrhiza glabra*, *Jasminum officinale*, *Picrorhiza kurrooa*, *Pongamia pinnata*, *Rubia cordifolia*, *Saussurea lappa*, *Terminalia chebula*, *Trichosanthes diocia* (6-9%, preferably 7%), *Capsicum* and *Stellata-Wild*.
 c) Suitable adjuncts include thickening agents, preservatives, coloring agents, fragrances and opacifiers The appropriate part of the herb used in the formulation is given below:

| S. No. | Scientific Name | Part Used in formulation |
| --- | --- | --- |
| 1. | Azadirachta indica | Bark |
| 2. | Berberis vulgaris | — |
|  | Berberis aristata | Root |
| 3. | Curcuma longa | Whole root |
| 4. | Glycyrrhiza glabra | Stem |
| 5. | Jasminum officinale | Whole plant comprising of stem, leaves and flowers |
| 6. | Picrorhiza kurrooa | Rhizome (stem) |
| 7. | Pongamia pinnata | Seeds or leaves |
| 8. | Rubia cordifolia | Stem |
| 9. | Saussurea lappa | Rhizome |
| 10. | Terminalia chebula | Fruit |
| 11. | Trichosanthes diocia | Fruit or Leaves |
| 12. | Capsicum | Fruit |
| 13. | Stellata-Wild | Flower |

It will be appreciated by those skilled in the art that the above approximate weight percents are dependent generally on the expected potencies of the individual components, whereby the relative weight percents will vary sometimes substantially from the above individual amounts. It will be within the skilled person's knowledge with this disclosure that the objects of the present invention require the inclusion of each of the components in relative approximate weight percents above.

The easy commercial availability of all the ingredients, the ease of manufacturing of the extracts and the finished product provides a cheap and effective alternative wound healing therapy, which does not have undesirable side-effects.

Example 1

Preparation of Aqueous Extract

The bark of *Azadirachta indica* is weighed, then thoroughly washed in cold water to remove any dirt, soil, undesirable contaminants etc. Distilled or de-ionized water in a 16:1 dry weight ratio to the herb is then added and allowed to soak overnight. The mixture is then boiled vigorously to reduce the volume of water to $\frac{1}{4}^{th}$ the original quantity. The extract is then filtered to remove the unwanted insoluble material. The extract obtained is the aqueous extract and is reddish brown.

Preparation of the Oil Mix:

The twelve herbs as listed above in dry form are weighed in appropriate quantities and then thoroughly washed in cold water. These are then dried and powdered. The dry weight percentage of each herbs is 1% except for two herbs, *Curcuma longa* and *Trichosanthes diocia* where dry weight percentage is 7%. Four oils as mentioned above, are taken in equal ratios, mixed in a container and dried herbs in powdered form, added to the oil mix.

Preparation of the Formulation:

The aqueous extract is added to the oil mix and heated till all the water has evaporated. This step results in the entry of thermostable, water soluble compounds derived from the bark of *Azadirachta indica* into an oil mix phase, along with extracts of other herbs. To the hot formulation are added thickeners, present in amounts anywhere from about 1-7% by weight, preferably 2%. In the present formulation, bee-wax is used as the thickener. To protect the formulation from any harmful growths, suitable preservatives have to be added. These include alkyl esters of p-hydroxybenzoic acid, hydantoin derivatives, propionate salts, potassium sorbate, sodium benzoate. The use of copper sulphate at low concentrations, is also well-documented in ancient Indian medical texts (*Ayurveda*). In the present formulation, copper sulphate at 0.25% concentration is used. The formulation is allowed to cool and filtered using appropriate filters available commercially. The final formulation is yellowish-green.

Example 2

The clean dried bark of *Azadirachta indica* is weighed and soaked overnight in distilled or de-ionized water in a 16:1 dry weight ratio. The mixture is then boiled to reduce the volume of water to ¼$^{th}$ the original quantity. The extract is then filtered to remove the unwanted insoluble material. The extract obtained is the aqueous extract and is reddish brown.

Preparation of the Oil Mix:

The clean and dried herbs as listed above in specified weight ratios are powdered. Alcohol extract of all the herbs is prepared which is then de-colorized using activated charcoal and then filtered. This filtrate is mixed in four oils taken in equal ratios and mixed in a container Preparation of the Formulation:

The aqueous extract is added to the oil mix and heated till all the water and alcohol evaporated. To the hot formulation are added bee wax as thickener in an amount of 2% by weight and copper sulphate at 0.25% concentration as preservative. The formulation is allowed to cool and filtered using appropriate filters available commercially. The final formulation is almost colourless.

Additional herbs e.g. *Sumplocos racemosa* and *Ichnicarpus frutesscens* along with minor adjunct components may also be incorporated into preferred embodiments of the formulation. The adjunct components include coloring agents, fragrances and opacifiers. The effect on skin may also be enhanced by adding various vitamins e.g. A, C and B and nutrients which also serve as antioxidants to help prevent the emollient degradation of the formulation.

I claim:

1. A topical wound healing formulation comprising:
   i) 4 to 7% by weight of an aqueous extract of bark of *Azadirachta indica*;
   an oil mix consisting of a mixture of four oils, wherein the oils are castor oil, mustard oil, coconut oil and black sesame oil, in combination with 0.5 to 4% by weight of the following herbs:
   a) root of *Berberis aristata* or *Berberis vulgaris*,
   b) stem of *Glycyrrhiza glabra*,
   c) stem, leaves or flowers of *Jasminum officinale*,
   d) rhizomes of *Picrorhiza kurroa*,
   e) seeds or leaves of *Pongamia pinnata*,
   f) stem of *Rubia cordiflia*,
   g) rhizomes of *Saussurea lappa*,
   h) fruits of *Terminalia chebula*,
   i) fruits of *Capsicum*,
   j) flowers of *Stellata wild*;
   6-9% by weight of *Curcuma longa*; and
   6-9% by weight of fruits or leaves of *Tricosanthes diocia*; and
   iii) preservatives, and wherein said formulation further comprises one or more adjuncts selected from the group consisting of thickening agents, coloring agents, decolorizing agents, fragrances, opacifiers, vitamins and combinations thereof.

2. The formulation according to claim 1, wherein said oils are present in equal ratios.

3. The formulation according to claim 1, wherein said preservative comprise copper sulphate.

4. The formulation according to claim 1, wherein said thickening agents comprises bee wax.

5. The formulation according to claim 1, wherein said decolorizing agents comprise activated charcoal, Fuller's earth, or combinations thereof.

6. The formulation according to claim 1, wherein said adjuncts further comprise Calcium D-Saccharate.

7. The formulation according to claim 1, wherein said opacifiers comprise Serolite, Bentonite, Magnesium oxide, or combinations thereof.

8. The formulation according to claim 1, wherein said formulation comprises:
   0.25% by weight of said preservatives;
   1% to 7% by weight of said thickening agent.

* * * * *